US00PP17353P2

(12) United States Plant Patent
Reinhoud

(10) Patent No.: US PP17,353 P2
(45) Date of Patent: Jan. 9, 2007

(54) **NEW GUINEA *IMPATIENS* PLANT NAMED 'ODYPARNASSUS'**

(50) Latin Name: *Impatiens hawkeri*
Varietal Denomination: Odyparnassus

(75) Inventor: Poula Reinhoud, Leiden (NL)

(73) Assignees: Agrion B.V., DeKwakel (NL); Florema Young Plants B.V., Aalsmeer (NL)

( * ) Notice: Subject to any disclaimer, the term of this patent is extended or adjusted under 35 U.S.C. 154(b) by 39 days.

(21) Appl. No.: 11/146,206

(22) Filed: Jun. 6, 2005

(51) Int. Cl.
*A01H 5/00* (2006.01)

(52) U.S. Cl. ..... Plt./318
(58) Field of Classification Search ..... Plt./318
See application file for complete search history.

(56) References Cited

U.S. PATENT DOCUMENTS

| | | | | | |
|---|---|---|---|---|---|
| PP9,226 | P | * | 8/1995 | Dehan | Plt./318 |
| PP10,302 | P | * | 3/1998 | Kientzler | Plt./318 |
| PP10,321 | P | * | 4/1998 | Kientzler | Plt./318 |
| PP11,535 | P | * | 10/2000 | Kientzler | Plt./318 |
| PP12,567 | P2 | * | 4/2002 | Kientzler | Plt./318 |

OTHER PUBLICATIONS

UPOV ROM GITIM Computer Database, GTI Jouve Retrieval Software 2006/05 Citation for 'Odyparnassus'.*

* cited by examiner

*Primary Examiner*—Wendy Hass
(74) *Attorney, Agent, or Firm*—C. A. Whealy

(57) ABSTRACT

A new and distinct cultivar of New Guinea *Impatiens* plant named 'Odyparnassus', characterized by its upright, outwardly spreading and vigorous growth habit; freely branching and freely flowering habit; dark green-colored foliage; large, rounded, pink-colored flowers; and flowers that are positioned above or beyond the foliage.

1 Drawing Sheet

Botanical designation: *Impatiens hawkeri.*
Cultivar denomination: 'Odyparnassus'.

BACKGROUND OF THE INVENTION

The present Invention relates to a new and distinct cultivar of New Guinea *Impatiens* plant, botanically known as *Impatiens hawkeri*, and hereinafter referred to by the name 'Odyparnassus'.

The new *Impatiens* is a product of a planned breeding program conducted by the Inventor in Aalsmeer, The Netherlands. The objective of the breeding program was to create New Guinea *Impatiens* with large flowers, attractive flower coloration, good postproduction longevity and drought tolerance.

The new New Guinea *Impatiens* originated from a cross-pollination conducted in Aalsmeer, The Netherlands on May 16, 2001 of a proprietary selection of New Guinea *Impatiens* identified as code number 99023, not patented, as the female, or seed, parent with a proprietary selection of New Guinea *Impatiens* identified as code number 99015, not patented, as the male, or pollen, parent, The cultivar Odyparnassus was discovered and selected by the Inventor as a single plant within the progeny of the stated cross-pollination in a controlled environment in Aalsmeer, The Netherlands on Sep. 30, 2001.

Asexual reproduction of the new cultivar by terminal cuttings in Aalsmeer, The Netherlands since Feb. 17, 2002, has shown that the unique features of this new *Impatiens* are stable and reproduced true to type in successive generations.

SUMMARY OF THE INVENTION

The following traits have been repeatedly observed and are determined to be the unique characteristics of 'Odyparnassus'. These characteristics in combination distinguish 'Odyparnassus' as a new and distinct *Impatiens* cultivar:

1. Upright, outwardly spreading and vigorous growth habit.
2. Freely branching and freely flowering habit.
3. Dark green-colored foliage.
4. Large, rounded, pink-colored flowers.
5. Flowers that are positioned above or beyond the foliage.

Plants of the new *Impatiens* can be compared to plants of the female parent selection. In side-by-side comparisons conducted by the Inventor in Aalsmeer, The Netherlands, plants of the new *Impatiens* differed from plants of the female parent selection primarily in flower coloration as plants of the female parent selection had red-colored flowers. In addition plants of the new *Impatiens* had smaller leaves than plants of the female parent selection.

Plants of the new *Impatiens* can be compared to plants of the male parent selection. In side-by-side comparisons conducted by the Inventor in Aalsmeer, The Netherlands, plants of the new *Impatiens* differed from plants of the male parent selection primarily in flower coloration as plants of the male parent selection had pink and white bi-colored flowers.

Plants of the new *Impatiens* can also be compared to plants of the cultivar Neptis, disclosed in U.S. Plant Pat. No. 10,321. In side-by-side comparisons conducted by the Inventor in Aalsmeer, The Netherlands, plants of the new *Impatiens* differed from plants of the cultivar Neptis in the following characteristics:

1. Plants of the new *Impatiens* were not as broad as plants of the cultivar Neptis.
2. Plants of the new *Impatiens* had shorter internodes than plants of the cultivar Neptis.
3. Plants of the new *Impatiens* had narrower leaves with smaller petioles than plants of the cultivar Neptis.
4. Plants of the new *Impatiens* were more freely flowering than plants of the cultivar Neptis.
5. Plants of the new *Impatiens* and the cultivar Neptis differed in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Impatiens*. The photograph comprises a side perspective view of a typical flowering plant of 'Odyparnassus' grown in a container.

DETAILED BOTANICAL DESCRIPTION

The cultivar Odyparnassus has not been observed under all possible environmental conditions. The phenotype may vary somewhat with variations in environment such as temperature and light intensity, without, however, any variance in genotype.

The aforementioned photograph, following observations and measurements describe plants grown during the fall in De Kwakel, The Netherlands, under commercial production practice in a glass-covered greenhouse. Rooted young plants were planted in 13-cm containers and the aforementioned photograph and following observations and measurements were taken about 14 weeks later. During the production of the plants, day and night temperatures averaged 18° C. and light levels were about 200 W/m$^2$. In the following description, color references are made to The Royal Horticultural Society Colour Chart, 1995 Edition, except where general terms of ordinary dictionary significance are used.

Botanical classification: *Impatiens hawkeri* cultivar Odyparnassus.

Parentage:

*Female, or seed, parent.*—Proprietary selection of *Impatiens hawkeri* identified as code number 99023, not patented.

*Male, or pollen, parent.*—Proprietary selection of *Impatiens hawkeri* identified as code number 99015, not patented.

Propagation:

*Type cutting.*—Terminal tip cuttings.

*Time to initiate roots.*—About 8 to 9 days at 18° C. to 22° C.

*Time to produce a rooted young plant.*—About 16 days at 18° C. to 22° C.

*Root description.*—Fine; white in color.

*Rooting habit.*—Freely branching.

Plant description:

*General appearance.*—Upright, outwardly spreading and vigorous plant growth habit; freely branching and freely flowering habit.

*Plant height.*—About 20 cm.

*Plant diameter or spread.*—About 30 cm.

*Lateral branches.*—Quantity per plant: About seven. Length: About 11 cm. Diameter: About 7 mm. Internode length: About 4 cm. Texture: Smooth, glabrous. Color: Close to 146A blushed with close to 183A.

*Foliage description.*—Arrangement: Opposite or in whorls. Length: About 11 cm. Width: About 3.5 cm. Shape: Lanceolate. Apex: Acuminate. Base: Attenuate. Margin: Serrulate with ciliation. Texture, upper and lower surfaces: Smooth, glabrous. Color: Developing foliage, upper surface: 137A. Developing foliage, lower surface: 147C blushed with close to 183A. Fully expanded foliage, upper surface: Darker than 139A. Fully expanded foliage, lower surface: 139C blushed with close to 183A. Venation, upper surface: 181B. Venation, lower surface: 183B. Petiole: Length: About 2 cm. Diameter: About 3 mm. Texture, upper and lower surfaces: Smooth, glabrous. Color, upper and lower surfaces: 183A.

Flower description:

*Flower type and flowering habit.*—Single, large, flat, rounded, pink-colored flowers. Freely and continuously flowering; usually about six flowers per lateral branch. Flowers positioned above or beyond the foliage; flowers typically face parallel to the leaf canopy. Petals not persistent; gynoecium persistent. Flowers not fragrant.

*Flower longevity.*—Flowers last about one week on the plant.

*Flowering season.*—Year-round under greenhouse conditions. Plants begin flowering about ten weeks after planting.

*Flower buds.*—Length: About 2 cm. Diameter: About 1.2 cm. Shape: Ovoid. Color: 45A.

*Flower diameter.*—About 7 cm.

*Flower depth.*—About 5 mm.

*Petals.*—Quantity: Five per flower, imbricate. Length: About 3.5 cm. Width: About 3 cm. Shape: Oblanceolate to cordate. Apex: Emarginate. Base: Cuneate to obtuse. Margin: Entire. Texture, upper and lower surfaces: Smooth, glabrous; satiny. Color: When opening, upper surface: 55C. When opening, lower surface: 55C and 41C. Fully opened, upper surface: 55C; stripes upper banner splotch and eye, 51A to 51B. Fully opened, lower surface: 55C and 41C.

*Spur.*—Quantity: One per flower. Length: About 5 cm. Diameter: At apex: About 1 mm. At flower: About 1.3 mm. Aspect: Curved. Texture: Smooth, glabrous. Color: 55C.

*Sepals.*—Quantity: Two per flower. Length: About 1 cm. Width: About 5 mm. Shape: Ovate. Apex: Acuminate. Base: Obtuse. Margin: Entire. Texture, upper and lower surfaces: Smooth, glabrous. Color, upper and lower surfaces: Close to 146A blushed with 183A.

*Peduncles.*—Length: About 4 cm. Diameter: About 2 mm. Texture: Smooth, glabrous. Strength: Strong, flexible. Color: 139D.

*Reproductive organs.*—Androecium: Stamen number: Five fused at anthers, hooded; filaments free. Anther length: About 5 mm. Anther shape: Oval. Anther color: 4C. Pollen amount: Abundant. Pollen color: Close to 4D. Gynoecium: Pistil quantity: One per flower. Pistil length: About 5 mm. Stigma shape: Rounded. Stigma color: 62A. Style color: 59A. Ovary: Five-celled. Ovary color: Close to 146A.

*Seed/fruit.*—Seed and fruit development has not been observed.

Disease/pest resistance: Plants of the new *Impatiens* have not been observed to be resistant to pathogens and pests common to *Impatiens*.

Temperature tolerance: Plants of the new *Impatiens* have been observed to tolerate temperatures from 8° C. to 35° C.

It is claimed:

1. A new and distinct cultivar of New Guinea *Impatiens* plant named 'Odyparnassus', as illustrated and described.

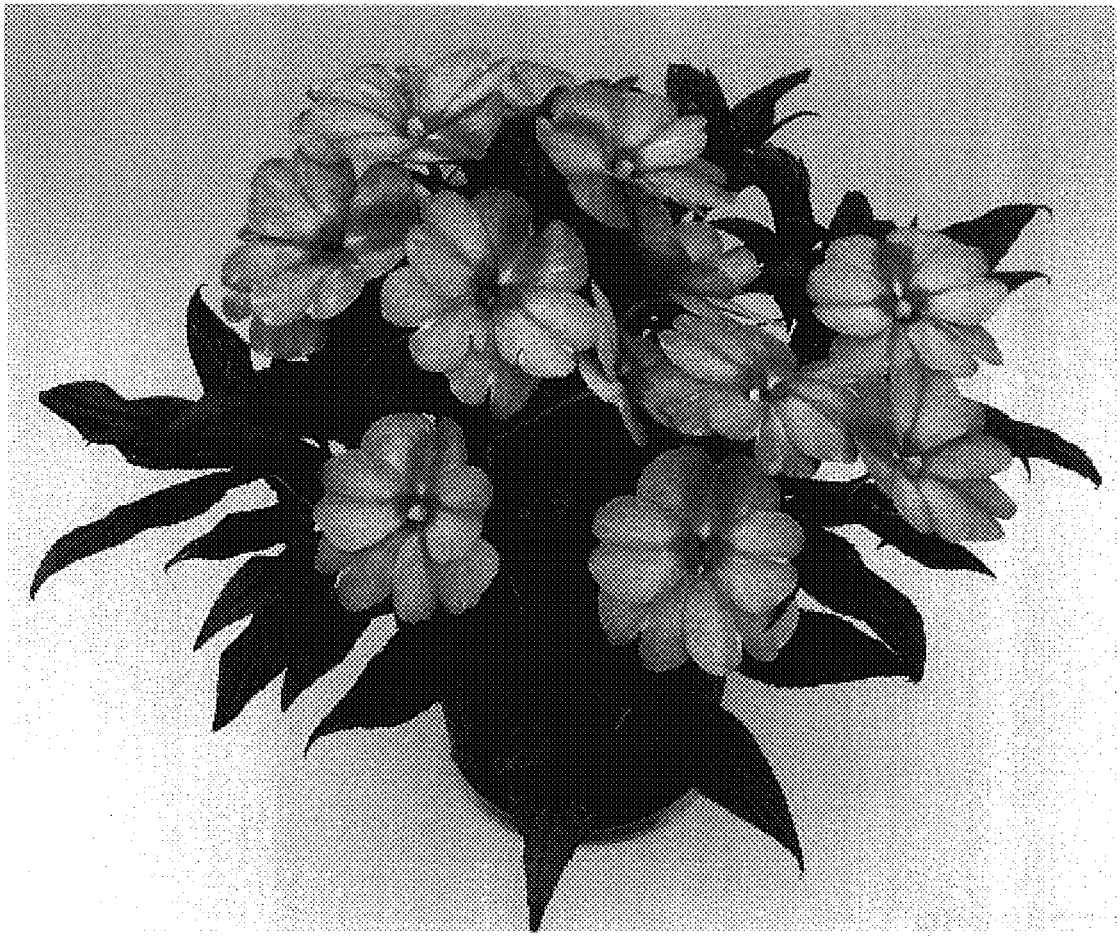

* * * * *